(12) United States Patent
Tsai et al.

(10) Patent No.: US 8,445,456 B2
(45) Date of Patent: May 21, 2013

(54) USE OF RNA INTERFERENCE FOR TREATING OR REDUCING PAIN

(75) Inventors: Ming-Dar Tsai, Taipei (TW); Yih-Jing Lee, New Taipei (TW)

(73) Assignees: Fu-Jen Catholic University, New Taipei (TW); Shin Kong Wu Ho Su Memorial Hospital, Taipei (TW)

( * ) Notice: Subject to any disclaimer, the term of this patent is extended or adjusted under 35 U.S.C. 154(b) by 0 days.

(21) Appl. No.: 13/182,707

(22) Filed: Jul. 14, 2011

(65) Prior Publication Data

US 2012/0289578 A1 Nov. 15, 2012

(51) Int. Cl.
*A61K 31/70* (2006.01)
*C07H 21/04* (2006.01)

(52) U.S. Cl.
USPC ...................................... 514/44 A; 536/24.5

(58) Field of Classification Search
None
See application file for complete search history.

(56) References Cited

U.S. PATENT DOCUMENTS

2011/0262386 A1* 10/2011 Bernhagen et al. .......... 424/85.2

OTHER PUBLICATIONS

Levy et al. Pain 2000, vol. 86, pp. 265-271.*
Lee et al. Molecular Immunology 2008, vol. 45, pp. 3693-3702.*
Fan et al., "RNA interference of bradykinin receptor reduces nociception on neuropathic pain models", Published Nov. 27-28, 2010.

* cited by examiner

*Primary Examiner* — Tracy Vivlemore
(74) *Attorney, Agent, or Firm* — Edwards Wildman Palmer LLP; Steven M. Jensen; Richard B. Emmons

(57) ABSTRACT

A use of a nucleic acid molecule mediating RNA interference for treating or reducing pain is disclosed. The nucleic acid molecule has a sequence selected from the group consisting of SEQ ID NO:1, SEQ ID NO:2, SEQ ID NO:3 and SEQ ID NO:4, and is used for effectively inhibiting expression of bradykinin B2 receptor, treating or reducing pain and preparing a pharmaceutical composition for reducing neuropathic pain.

6 Claims, 1 Drawing Sheet

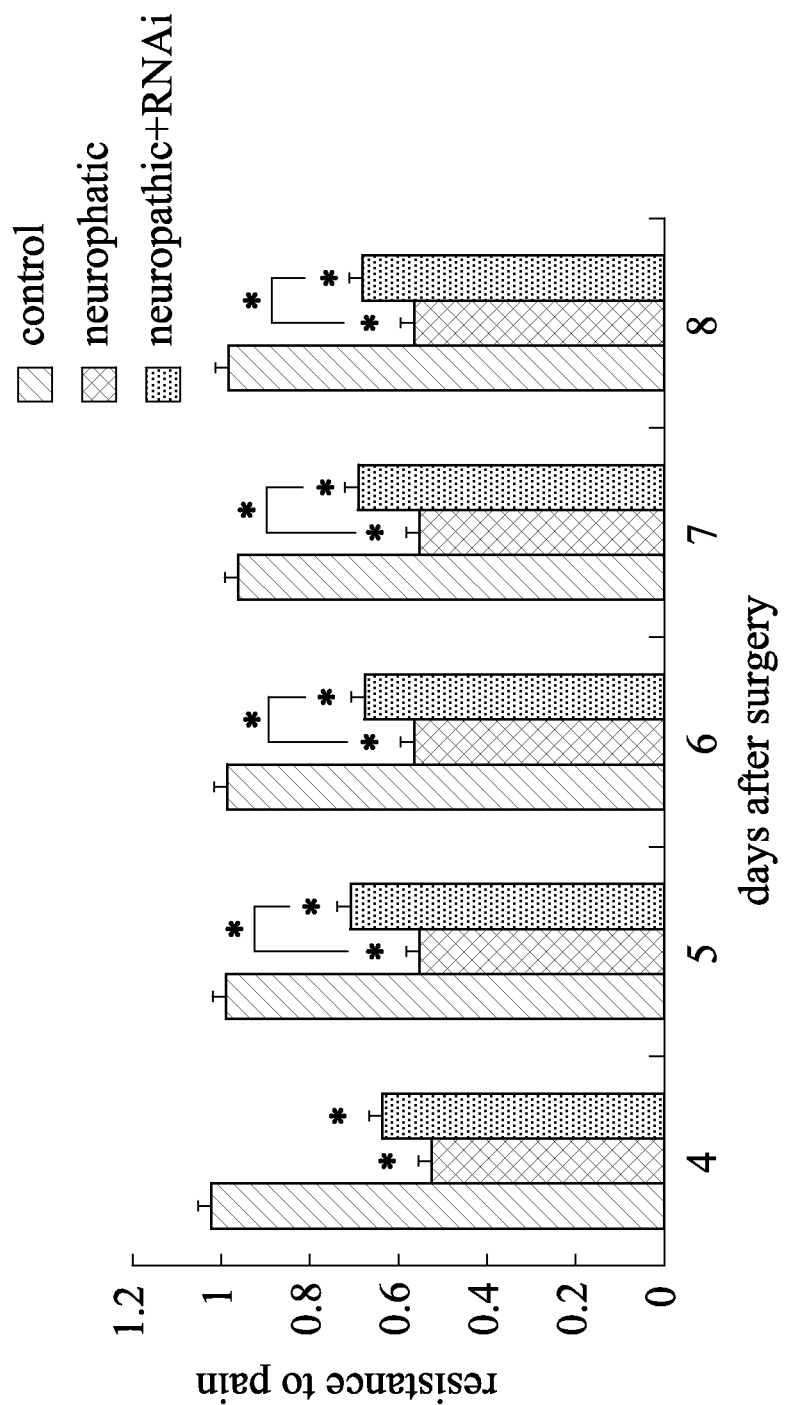

USE OF RNA INTERFERENCE FOR TREATING OR REDUCING PAIN

CROSS-REFERENCES TO RELATED APPLICATIONS

This application claims under 35 U.S.C. §119(a) the benefit of Taiwanese Application No. 100116272, filed May 10, 2011, the entire contents of which is incorporated herein by reference.

FIELD OF INVENTION

The present invention relates to a use of RNA interference for treating or reducing pain, and more particularly, to a use RNA interference for treating or reducing neuropathic pain.

SEQUENCE LISTING

The instant application contains a Sequence Listing which has been submitted in ASCII format via EFS-Web, and is hereby incorporated by reference in its entirety. Said ASCII copy, created on Dec. 22, 2011, is named 8893671987-88936719_1.txt and is 1,239 bytes in size.

BACKGROUND OF THE INVENTION

Pain is a complicate neural reaction mediated by nociceptors in response to physical, temperature and chemical stimuli. Damage stimuli such as inflammation, tissue necrosis, ischemia or anoxaemia, release some cytokine or body fluid to activate nociceptors, so as to cause pain. The cytokine or body fluid may be acetylcholine, 5-hydroxy tryptamine, histamine, bradykinin, prostaglandin, potassium ion, hydrogen ion or acidic products resulting from tissue damages.

Bradykinin is a peptide and a strong mediator in the mechanism of inflammation and pain. Bradykinin is an activator of B2 receptor of the neuron responsible for sense of pain. Thus, while blocking the bradykinin B2 receptor, the sense of pain is inactivated.

Neuropathic pain is pain resulting from abnormal neuron system such as neural inflammation or neural damage. For example, herpes zoster is a viral disease characterized by neural inflammation and a painful skin rash. The pain continues even the skin rash disappears, and is thus called as post-herpetic neuralgia. In addition, patients with trigeminal neuralgia, diabetes, stroke, injured intrathecal cord, injured peripheral nerve system, amputation or carpal tunnel syndrome may have neuralgia. Further, neuralgia may occur due to a pressed or injured nerve resulting from a broken bone, intervertebral disk herniation or a tumor.

However, neuropathic pain has poor response to the conventional analgesics. Moreover, the chronic neuropathic pain is commonly associated with syndromes such as sleeplessness, anxiety, melancholia and the like, such that the patient, family and society suffer severely.

Accordingly, there is an urgent to develop a method for treating or reducing pain, especially neuropathic pain.

SUMMARY OF THE INVENTION

It is an aspect of the present invention to provide a use of a nucleic acid molecule mediating RNA interference for treating or reducing pain, wherein the nucleic acid molecule has a sequence selected from the group consisting of SEQ ID NO:1, SEQ ID NO:2, SEQ ID NO:3 and SEQ ID NO:4 for effectively inhibiting expression of bradykinin B2 receptor, so as to treat or reduce neuropathic pain or prepare pharmaceutical composition for reducing neuropathic pain.

It is another aspect of the present invention to provide a use of a nucleic acid molecule mediating RNA interference for preparing a pharmaceutical composition for reducing pain, wherein the pharmaceutical composition includes an active component, which is the nucleic acid molecule having a sequence selected from the group consisting of SEQ ID NO:1, SEQ ID NO:2, SEQ ID NO:3 and SEQ ID NO:4, and the pharmaceutical composition optionally includes a pharmaceutical acceptable carrier.

It is another aspect of the present invention to provide a pharmaceutical composition for treating or reducing pain. The pharmaceutical composition includes an active component, which is the nucleic acid molecule having a sequence selected from the group consisting of SEQ ID NO:1, SEQ ID NO:2, SEQ ID NO:3 and SEQ ID NO:4, and the pharmaceutical composition optionally includes a pharmaceutical acceptable carrier.

It is another aspect of the present invention to provide a use of a nucleic acid molecule mediating RNA interference for preparing a pharmaceutical composition for reducing pain, wherein the pharmaceutical composition comprises an active component, which is the nucleic acid molecule having a sequence selected from the group consisting of SEQ ID NO:1, SEQ ID NO:2, SEQ ID NO:3 and SEQ ID NO:4, and the pharmaceutical composition optionally includes a pharmaceutical acceptable carrier.

It is another aspect of the present invention to provide a method for treating or reducing pain. The method includes the step of using a nucleic acid molecule mediating RNA interference for inhibiting expression of bradykinin B2 receptor, thereby treating or reducing pain. The nucleic acid molecule has a sequence selected from the group consisting of SEQ ID NO:1, SEQ ID NO:2, SEQ ID NO:3 and SEQ ID NO:4. The nucleic acid molecule is administrated to a patient by intravenous administration, intrathecal administration, periganglionic injection, intraventrical injection, intraparenchymal injection, intramuscular injection or intradermal injection.

BRIEF DESCRIPTION OF THE DRAWINGS

FIG. 1 is a diagram showing the result of the mechanical pressure test (von Frey's test) in the present invention.

DETAILED DESCRIPTION OF THE PREFERRED EMBODIMENTS

RNA interference is one of the gene regulations in a cell, wherein gene expression is regulated by degradation of mRNA mediated by double-stranded RNA (dsRNA). The ribonuclease protein Dicer binds and cleaves double-stranded RNAs (dsRNAs) to produce double-stranded fragments of 19-25 base pairs (small interfering RNA, siRNAs). The siRNAs are coupled with RNA-induced silencing complex (RISC), then unwound into single strands, and specifically bind to target nucleic acid, so as to specifically regulates gene expression, i.e. post transcriptional gene silencing.

siRNAs may be transfected into cells to knock-down specific genes and to cause gene silencing, such that siRNAs are important tools for studying gene functions and drug targets. siRNAs have been used for treating diseases such as age-related macular degeneration, amyotrophic lateral sclerosis, rheumatoid arthritis, obesity and etc. Further, siRNAs are used for tumor treatment and antiviral treatment such as treating Parkinson's disease. However, siRNAs have not been used for effectively treating pain, and especially for treating neuropathic pain associated with expression of bradykinin B2 receptor.

In the present invention, siRNAs, especially siRNAs having 19-25 base pairs, are used for inhibiting expression of bradykinin B2 receptor, so as to treat or reduce pain such as neuropathic pain. Alternatively, the siRNAs of the present invention may be used for preparing a pharmaceutical composition for treating or reducing pain such as neuropathic pain. In the present invention, the siRNAs may be single stranded siRNAs or double stranded siRNAs. At least one strand of the siRNAs has the sequence SEQ ID NO:1, SEQ ID NO:2, SEQ ID NO:3 or SEQ ID NO:4.

SEQ ID NO: 1
5'- GCACUGUGGCUGAGAUCUA-3'

SEQ ID NO: 2
5'- GAACGAGCGUGCCGUGGAU-3'

SEQ ID NO: 3
5'- GUUCCUACGUGGCCUAUAG-3'

SEQ ID NO: 4
5'- UGGUGAACACUAUGAUAUA-3'

In one embodiment, the pharmaceutical composition of the present invention includes a mixture of siRNAs having the sequence SEQ ID NO:1, SEQ ID NO:2, SEQ ID NO:3 and SEQ ID: NO:4. In the embodiment, the ratios of the siRNA having the sequence SEQ ID NO:1, the siRNA having the sequence SEQ ID NO:2, the siRNA having the sequence SEQ ID NO:3 and the siRNA having the sequence SEQ ID NO:4 are 0.5-1.5:0.5-1.5:0.5-1.5:0.5-1.5 in the mixture. Preferably, the ratios of the siRNA having the sequence SEQ ID NO:1, the siRNA having the sequence SEQ ID NO:2, the siRNA having the sequence SEQ ID NO:3 and the siRNA having the sequence SEQ ID NO:4 are 1:1:1:1 in the mixture.

In addition, the siRNA of the present invention further includes siRNAs complementary to at least 80% of the mRNA, which is the target of the sequence SEQ ID NO:1, SEQ ID NO:2, SEQ ID NO:3 or SEQ ID NO:4.

The siRNAs of the present invention may be formed by chemical synthesis, and 5' end of one or both strands may be optionally phosphorylated to enhance the efficiency of RNA interference.

In one embodiment, the siRNAs are used for treating or reducing pain, in which the pharmaceutical composition may include the siRNA having the sequence SEQ ID NO:1, SEQ ID NO:2, SEQ ID NO:3 or SEQ ID NO:4, optionally a pharmaceutical acceptable carrier such as water, a buffer, a salt, glycine, glycerol, hyaluronic acid or mannitol, medium, a transfection reagent; and the pharmaceutical composition is administrated to a patient by intravenous administration, intrathecal administration, periganglionic injection, intraventrical injection, intraparenchymal injection, intramuscular injection or intradermal injection.

The features and effects of the present invention are illustrated by, but not limited to, the following examples. A person skilled in the art can easily conceive the other advantages and effects of the present invention.

EMBODIMENTS

Preparation

Single stranded siRNAs (a mixture of sequences SEQ ID NO: 1, SEQ ID NO:2, SEQ ID NO:3 and SEQ ID NO:4) which are formed by chemical synthesis, were suspended in physiological saline. The stock concentration was 200 µM, which was diluted to 200 nM for use and mixed with 155 µl of the medium and 7.5 µl of the transfection reagent (oligofectamine). The mixture was incubated for 24 hours to form Sample 1.

Embodiment 1

The Sprague-Dawley rats (200-250 g) were fed under the condition of 12 hour light and 12 hour dark (12L-12D) in the pathogen controlled environment, fully supplied with water and allowed to free intake. The surgery and experiments were performed according to L5/L6 nerve ligation model (Kim and Chung et al., 1992). After being weighted, the Sprague-Dawley rats were anesthetized by intraperitoneal injection of chloral hydrate (RDH, 0.4 g/ml i.p.). In the surgery, the sciatic nerve, ural, common peroneal and tibial nerves were exposed on left legs, the L5 spinal nerve was clipped by the premium surgiclip, and the muscle and epidermis were sutured. After the wound healed, the rats were on the heating blanket to recover. The rats were grouped into two groups. The L5 spinal nerve ligation was performed in the control group. In the experiment group, the L5 spinal nerve ligation was performed, Sample 1 (200 µl) was immediately administered at the left lumbar, and then Sample 1 was administrated every 2-3 days. The pain sensory was evaluated after one week upon surgery.

Before basic tests, all the rats were fed in the test environment for 3-7 days. The temperature and humidity of the test environment were kept stable.

The electronic von Frey anesthesiometer (IITC Life Science, mold: 2390) was used for mechanical allodynia. The single fiber used in the test was 800 gm rigid tip. The sciatic nerve areas of hind paws of the rats were tested. The rats were placed on the wire mesh in the plastic cage, and then tested after being calm for 5-10 minutes. The threshold stimulus was determined based on paw-jerks while stabbing middle tibial zone of the hind paw of the rat. The right hind paw was stabbed, and then the left hind paw was stabbed. When the paw was stab, the rat may lick or bite the paw, or move the body toward the paw. The experiment was repeated for 11 times, and the results were shown in Table 1 and FIG. 1.

TABLE 1

| Days after surgery | Resistance (mean ± SEM) | | |
|---|---|---|---|
| | Control group | Neuropathic group | Neuropathic + RNAi group |
| 4 | 102.7 ± 3.4% | 52.8 ± 4.9% | 64.4 ± 5.4% |
| 5 | 99.9 ± 4.3% | 55.4 ± 3.5% | 71.4 ± 2.4% |
| 6 | 99.6 ± 3.2% | 56.5 ± 3.6% | 68.2 ± 2.7% |
| 7 | 97.2 ± 2.8% | 55.7 ± 3.6% | 69.6 ± 3.9% |
| 8 | 99.0 ± 2.9% | 57.2 ± 4.0% | 68.7 ± 3.2% |

While having pain, the animals had lower tolerance in response to stimulus, such that the lower value indicated poor tolerance. In the experiments, the resistance was represented with percentage (%). Since every animal had different tolerance to pain (stimulus), the resistance of each paw to the stimulus before the surgery and any treatment was determined as 100%. The rats were grouped into the control group without any treatment, the neuropathic group having the nerve ligation, and the neuropathic+RNAi group having the nerve ligation and the RNA interference treatment.

The experiment data were analyzed with single factor analysis of variances and Bonferroni method, and * indicated the significant variation $p<0.05$ in comparison with the control group. The results showed that the nerve ligation increased the level of pain to the rats; however, the resistance to pain was increased due to the treatment of the RNA interference treatment. Accordingly, the present invention relieves or reduces pain.

The invention has been described using exemplary preferred embodiments. However, it is to be understood that the scope of the invention is not limited to the disclosed arrangements. The scope of the claims, therefore, should be accorded the broadest interpretation, so as to encompass all such modifications and similar arrangements.

2. The method of claim 1, wherein the pain is neuropathic pain.

3. The method of claim 1, wherein the nucleic acid molecule is administrated to a patient by injection.

4. The method of claim 1, the nucleic acid molecule is administrated to a patient by intravenous administration, intrathecal administration, periganglionic injection, intraventrical injection, intraparenchymal injection, intramuscular injection, or intradermal injection.

What is claimed is:

1. A method for treating or reducing pain, comprising the step of: using a nucleic acid molecule mediating RNA interference for inhibiting expression of bradykinin B2 receptor, thereby treating or reducing pain, wherein the nucleic acid molecule has a sequence selected from the group consisting of SEQ ID NO:1, SEQ ID NO:2, SEQ ID NO:3, and SEQ ID NO:4.

5. A pharmaceutical composition for treating or reducing pain, comprising: an active component, which is a nucleic acid molecule having a sequence selected from the group consisting of SEQ ID NO:1, SEQ ID NO:2, SEQ ID NO:3 and SEQ ID NO:4.

6. The pharmaceutical composition of claim 5, further comprising a pharmaceutical acceptable carrier.

* * * * *

SEQUENCE LISTING

```
<160> NUMBER OF SEQ ID NOS: 4

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
gcacuguggc ugagaucua                                                19

<210> SEQ ID NO 2
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
gaacgagcgu gccguggau                                                19

<210> SEQ ID NO 3
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
guuccuacgu ggccuauag                                                19

<210> SEQ ID NO 4
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
uggugaacac uaugauaua                                                19
```